(12) United States Patent
Gono

(10) Patent No.: US 9,084,534 B2
(45) Date of Patent: Jul. 21, 2015

(54) OPTICAL MEASUREMENT APPARATUS, ENDOSCOPE SYSTEM, AND COMPUTER READABLE STORAGE MEDIUM

(71) Applicant: OLYMPUS MEDICAL SYSTEMS CORP., Tokyo (JP)

(72) Inventor: Kazuhiro Gono, Sagamihara (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 322 days.

(21) Appl. No.: 13/679,603

(22) Filed: Nov. 16, 2012

(65) Prior Publication Data

US 2013/0123644 A1    May 16, 2013

Related U.S. Application Data

(63) Continuation of application No. PCT/JP2012/060370, filed on Apr. 17, 2012.

(60) Provisional application No. 61/476,439, filed on Apr. 18, 2011.

(51) Int. Cl.
*A61B 8/14*    (2006.01)
*A61B 5/00*    (2006.01)
*A61B 1/00*    (2006.01)
(Continued)

(52) U.S. Cl.
CPC .......... *A61B 5/0084* (2013.01); *A61B 1/00006* (2013.01); *A61B 1/00043* (2013.01); *A61B 1/018* (2013.01); *A61B 1/05* (2013.01); *A61B 5/7221* (2013.01); *G02B 23/2484* (2013.01); *A61B 5/1459* (2013.01)

(58) Field of Classification Search
None
See application file for complete search history.

(56) References Cited

U.S. PATENT DOCUMENTS

| 5,617,136 A | 4/1997 | Iso et al. |
| 7,051,309 B1 * | 5/2006 | Crosetto ................. 716/122 |

(Continued)

FOREIGN PATENT DOCUMENTS

| CN | 1531410 A | 9/2004 |
| JP | A-07-289507 | 11/1995 |

(Continued)

OTHER PUBLICATIONS

Aug. 19, 2014 European Search Report issued in EP 12774884.6.
(Continued)

*Primary Examiner* — Unsu Jung
*Assistant Examiner* — Joseph M Santos Rodriguez
(74) *Attorney, Agent, or Firm* — Oliff PLC

(57) ABSTRACT

An optical measurement apparatus of the present invention includes a light source unit; an operation unit that performs an operation process on the basis of a result of the measurement performed by a measurement unit to obtain a characteristic value of a living tissue; a validity evaluator that evaluates, on the basis of an operation result of the operation process performed by the operation unit, whether the result of the measurement is valid; an output unit that outputs a result of the evaluation performed by the validity evaluator; an input unit that inputs an instruction to adopt the result of the measurement performed by the measurement unit; and a determination unit that determines, on the basis of the result of the evaluation performed by the validity evaluator and the instruction information from the input unit, whether to adopt the result of the measurement performed by the measurement unit.

5 Claims, 11 Drawing Sheets

(51) Int. Cl.
*A61B 1/018* (2006.01)
*A61B 1/05* (2006.01)
*G02B 23/24* (2006.01)
*A61B 5/1459* (2006.01)

(56) References Cited

U.S. PATENT DOCUMENTS

| | | |
|---|---|---|
| 7,058,441 B2 | 6/2006 | Shahar et al. |
| 7,229,407 B2 * | 6/2007 | Suzushima ............. 600/179 |
| 7,652,881 B1 | 1/2010 | Sun |
| 2001/0016680 A1 | 8/2001 | Minami et al. |
| 2002/0087084 A1 | 7/2002 | Shahar et al. |
| 2008/0037024 A1 | 2/2008 | Backman et al. |
| 2009/0003759 A1 | 1/2009 | Boyd |
| 2009/0009759 A1 | 1/2009 | Backman et al. |
| 2009/0124853 A1 | 5/2009 | Gono et al. |
| 2009/0124874 A1 | 5/2009 | Gono et al. |
| 2009/0306522 A1 | 12/2009 | Gono et al. |

FOREIGN PATENT DOCUMENTS

| | | |
|---|---|---|
| JP | A-10-323326 | 12/1998 |
| JP | A-2000-014629 | 1/2000 |
| JP | A-2001-228412 | 8/2001 |
| JP | A-2006-296858 | 11/2006 |
| JP | A-2011-502555 | 1/2011 |
| JP | A-2011-521672 | 7/2011 |
| WO | WO 2007/133684 A2 | 11/2007 |
| WO | WO 2009/061009 A1 | 5/2009 |
| WO | WO 2009/148187 A1 | 12/2009 |

OTHER PUBLICATIONS

May 29, 2012 International Search Report issued in Application No. PCT/JP2012/060370 (with translation).

Jan. 29, 2013 Japanese Office Action issued in Japanese Application No. 2012-549586 (with translation).

Nov. 28, 2014 Office Action issued in Chinese Application No. 201280004204.1.

* cited by examiner

OPTICAL MEASUREMENT APPARATUS, ENDOSCOPE SYSTEM, AND COMPUTER READABLE STORAGE MEDIUM

CROSS-REFERENCE TO RELATED APPLICATIONS

This application is a continuation of PCT International Application No. PCT/JP2012/060370, filed on Apr. 17, 2012, which designates the United States, incorporated herein by reference, and which claims the benefit of priority from U.S. Provisional Patent Application No. 61/476,439, filed on Apr. 18, 2011.

BACKGROUND OF THE INVENTION

1. Field of the Invention

The present invention relates to an optical measurement apparatus, an endoscope system, and a computer-readable storage medium.

2. Description of the Related Art

In recent years, optical measurement apparatuses have been proposed that use low-coherence enhanced backscattering (LEBS) technology to radiate incoherent light that has a low spatial coherence from the distal end of a probe at a living tissue, which functions as a scatterer, and then measure the intensity distribution of the scattering light so that the properties of the scatterer can be detected (for example, International Publication No. WO 2007/133684, the specification of U.S. Laid-open Patent Publication No. 2008/0037024, the specification of U.S. Pat. No. 7,652,881, and the specification of U.S. Laid-open Patent Publication No. 2009/0003759). Such an optical measurement apparatus is combined with an endoscope to observe internal organs, such as the digestive organs, and thus performs optical measurement on a subject, such as living tissue functioning as a scatterer.

An optical measurement apparatus using the LEBS technology measures the intensity distribution of scattering light from the living tissue by obtaining, using a light receiving fiber, scattering light with desired multiple angles and performs, on the basis of the result of the measurement, multiple types of operation processes, thereby obtaining values for the living tissue's properties.

SUMMARY OF THE INVENTION

An optical measurement apparatus according to one aspect of the present invention is an optical measurement apparatus for measuring an optical characteristic of a living tissue. The optical measurement apparatus includes: a light source unit that supplies irradiation light to be emitted to the living tissue; a measurement unit that measures reflection light and/or scattering light from the living tissue; an operation unit that performs an operation process on the basis of a result of the measurement performed by the measurement unit to obtain a characteristic value of the living tissue; a validity evaluator that evaluates, on the basis of an operation result useful for validity evaluation in middle of the operation process performed by the operation unit, whether the result of the measurement performed by the measurement unit is valid; an output unit that outputs at least a result of the evaluation performed by the validity evaluator; an input unit that inputs instruction information containing an instruction to adopt the result of the measurement performed by the measurement unit; and a determination unit that determines, on the basis of the result of the evaluation performed by the validity evaluator and the instruction information input by the input unit, whether to adopt the result of the measurement performed by the measurement unit.

Moreover, an endoscope system according to another aspect of the present invention includes an endoscope that includes an imaging unit provided at a distal end and includes a channel provided internally; an optical measurement apparatus that includes a probe of which a distal end is inserted into a subject via the channel of the endoscope and includes a main body device to which the probe is detachably attached; a light source device that supplies light to irradiate an imaging field of the imaging unit; a signal processing device that processes a signal of an image captured by the imaging unit; and a display device that displays the image processed by the signal processing device. The main body device includes a light source unit that supplies irradiation light to be emitted to the living tissue; a measurement unit that measures reflection light and/or scattering light from the living tissue; an operation unit that performs an operation process on the basis of a result of the measurement performed by the measurement unit to obtain a characteristic value of the living tissue; a validity evaluator that evaluates, on the basis of an operation result useful for validity evaluation in middle of the operation process performed by the operation unit, whether the result of the measurement performed by the measurement unit is valid; an output unit that outputs at least a result of the evaluation performed by the validity evaluator; an input unit that inputs instruction information containing an instruction to adopt the result of the measurement performed by the measurement unit; and a determination unit that determines, on the basis of the result of the evaluation performed by the validity evaluator and the instruction information input by the input unit, whether to adopt the result of the measurement performed by the measurement unit. The probe includes an irradiation fiber for transferring the light supplied by the light source unit to emit the light to the living tissue and a light receiving fiber for receiving the reflection light and/or the scattering light from the living tissue to output the reflection light and/or the scattering light to the measurement unit.

Moreover, a computer-readable storage medium according to another aspect of the present invention causes a processor of an optical measurement process for measuring an optical characteristic of a living tissue to perform a measuring step of causing a light source device to emit light to the living tissue and measuring reflection light and/or scattering light from the living tissue; an operation step of performing an operation process on the basis of a result of the measuring at the measuring step to obtain a characteristic value of the living tissue; a validity evaluating step of evaluating, on the basis of an operation result useful for validity evaluation in middle of the operation process at the operation step, whether the result of the measuring at the measuring step is valid; an outputting step of outputting at least a result of the evaluating at the validity evaluating step; an inputting step of inputting instruction information containing an instruction to adopt the result of the measuring performed at the measuring step; and a determining step of determining, on the basis of the result of the evaluating at the validity evaluating step and the instruction information input at the inputting step, whether to adopt the result of the measuring at the measuring step.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Preferred embodiments of an optical measurement apparatus, an endoscope system, and an optical measurement program according to the present invention will be described in detail below with reference to the drawings. Note that the embodiments do not limit the present invention. The same or like parts are designated by the same reference numbers throughout the drawings.

Figure 1:
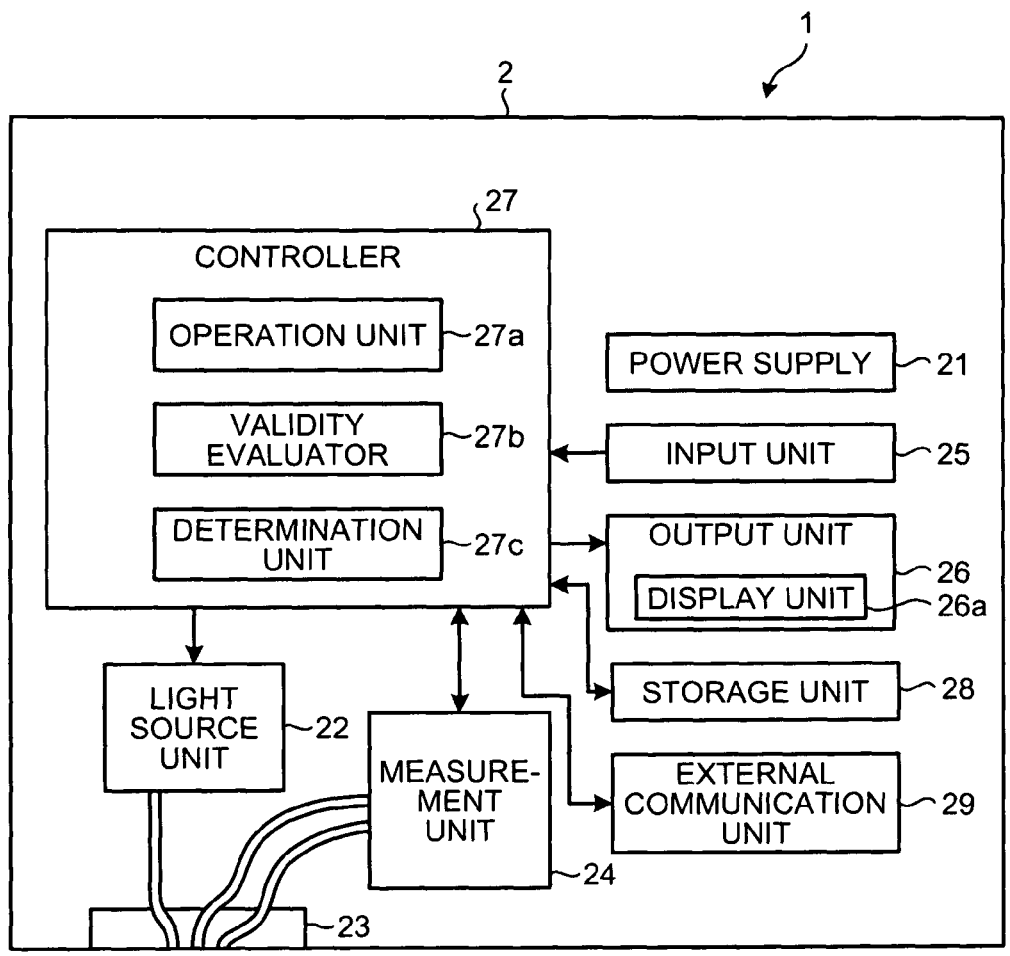
FIG. 1 is a schematic diagram of a schematic configuration of an optical measurement apparatus according to an embodiment.
Figure 1:
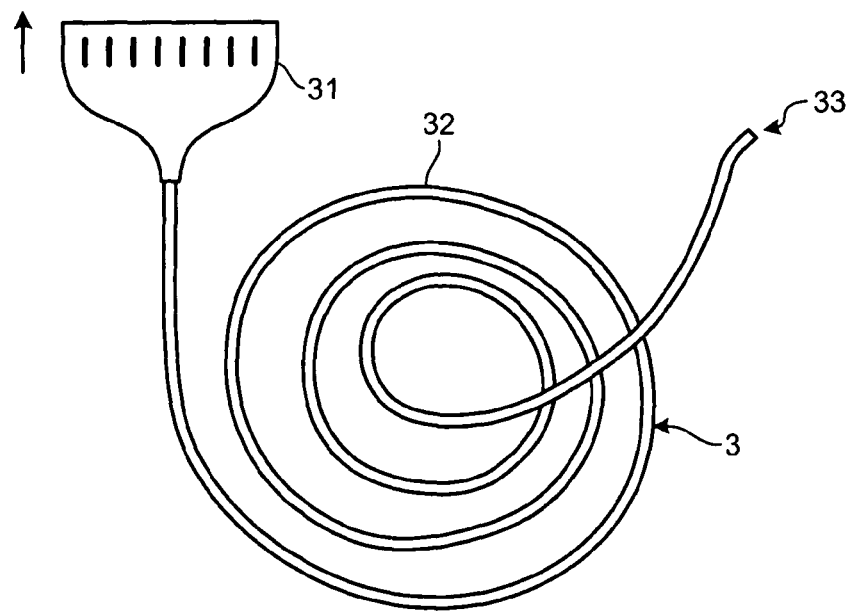

FIG. 1 is a schematic diagram of a schematic configuration of an optical measurement apparatus according to an embodiment of the present invention.

As shown in FIG. 1, an optical measurement apparatus 1 according to the embodiment includes a main body device 2 that performs optical measurement on a living tissue and performs an operation to obtain a characteristic value of the living tissue that functions as a scatterer and on which the measurement is performed; and a probe 3 that is inserted into the living tissue. The probe 3 emits light, which is supplied from the proximal end, at the measurement target from its distal end and outputs, from its proximal end to the main body device 2, the reflection light or scattering light returned from the living tissue and incident on the distal end.

The main body device 2 includes a power supply 21, a light source unit 22, a connector 23, a measurement unit 24, an input unit 25, an output unit 26, a controller 27, a storage unit 28, and an external communication unit 29.

The power supply 21 supplies power to each component of the main body device 2.

The light source unit 22 emits light to irradiate a living tissue. The light source unit 22 is implemented using an incoherent light source, such as a white light emitting diode (LED), a xenon lamp, or a halogen lamp, and one or more lenses. The light source unit 22 supplies incoherent light to the probe 3 at a predetermined timing.

The connector 23 detachably connects the proximal end of the probe 3 to the main body device 2. The connector 23 supplies, to the probe 3, light emitted by the light source unit 22 and outputs, to the measurement unit 24, the scattering light output from the probe 3.

The measurement unit 24 measures the light that is output from the probe 3 and then returned from the living tissue. The measurement unit 24 is implemented using a spectrometer. The measurement unit 24 performs measurement of each wavelength by measuring the spectral components and intensity of the returned light output from the probe 3. The measurement unit 24 outputs the result of the measurement to the controller 27. The measurement unit 24 repeatedly performs a process to measure the returned light at a predetermined measurement timing corresponding to a light emitting process performed by the light source unit 22.

The input unit 25 is implemented using, for example, a push switch. The switch is operated so that the input unit 25 accepts instruction information that contains an instruction to start the main body device 2 or other various types of instruction information and inputs the information to the controller 27.

The output unit 26 outputs information on various types of processes performed by the optical measurement apparatus 1. The output unit 26 includes a display unit 26a consisting of a display. The output unit 26 is implemented using a speaker, a motor, or the like. The output unit 26 may output information on the various types of processes performed by the optical measurement apparatus 1 by outputting image information, audio information, or vibrations.

The controller 27 controls process operations of each component of the main body device 2. The controller 27 is realized using a central processing unit (CPU) and a semiconductor memory such as a random access memory (RAM). The controller 27 controls operations of the main body device 2 by transferring instruction information and data to each component of the main body device 2.

The controller 27 includes an operation unit 27a, a validity evaluator 27b, and a determination unit 27c.

On the basis of the result of the measurement performed by the measurement unit 24, the operation unit 27a performs multiple types of operation processes to perform an operation to obtain a characteristic value of the living tissue. The operation unit 27a performs operation processes that includes, for example, a process to correct the intensity distribution of the light returned from the living tissue, the intensity distribution being measured by the measurement unit 24; an operation process to obtain reflectance; an integral process performed on the intensity of the returned light in a predetermine wavelength range; an inter-wavelength operation process to obtain a slope of a signal waveform; Fourier analysis to obtain the frequency of the waveform; an intensity ratio obtaining process to obtain the intensity ratio between two predetermined wavelengths; an operation process to obtain a correlation with a well-known hemoglobin waveform, which is a process performed in order to obtain the amount of hemoglobin; an operation process to obtain a scattering coefficient and an operation process to obtain an absorption coefficient, which are processes using the Monte Carlo method; an operation process to obtain the size of a cell nucleus by using the Mie scattering method; and an operation process to obtain the amount of chromatin. The type of the characteristic value that is obtained by the operation unit 27a by performing an operation is set, for example, according to instruction information input from the input unit 25 by an operator's operation.

On the basis of the operation result of any one of the multiple types of operation process performed by the operation unit 27a, the validity evaluator 27b evaluates whether the result of the measurement performed by the measurement unit 24 is valid. The validity evaluator 27b evaluates whether the measurement result is valid by comparing a threshold, which is set beforehand on the basis of a operation result determined to be valid, with the operation result of any one of the multiple types of operation processes. Alternatively, the validity evaluator 27b evaluates whether the measurement result is valid by comparing an acceptable range, which is set beforehand on the basis of multiple operation results determined to be valid, with the operation result of any one of the multiple types of operation processes. In the present embodiment, the validity evaluator 27b evaluates the validity of the characteristic value that is set as the characteristic value to be finally obtained.

The result of the evaluation performed by the validity evaluator 27b is output by the output unit 26. The operator confirms the result of the validity evaluation on the measurement result, which is the result of the validity evaluation output by the output unit 26 and operates the input unit 25 so as it adopts the measurement result. According to the operator's operation, the input unit 25 inputs instruction information containing an instruction to adopt the measurement result.

On the basis of the result of the evaluation performed by the validity evaluator 27b and the instruction information input from the input unit 25, the determination unit 27c determines whether to adopt the result of the measurement performed by the measurement unit 24. When instruction information containing an instruction to adopt the measurement result is input from the input unit 25, the determination unit 27c adopts the measurement result regardless of the result of the evaluation performed by the validity evaluator 27b. In other words, if instruction information containing an instruction to adopt the measurement result is input from the input unit 25, the determination unit 27c adopts even a measurement result that is evaluated to be invalid by the validity evaluator 27b. If no instruction information containing an instruction to adopt the measurement result is input from the input unit, the validity evaluator 27b does not adopt any measurement result regardless of the result of the validity evaluation performed by the validity evaluator 27b.

When the determination unit 27c determines that the measurement result is to be adopted, the operation unit 27a performs an operation to obtain a characteristic value based on the measurement result that is the last measurement result determined to be adopted among the measurement results that are evaluated as valid by the validity evaluator 27b. The output unit 26 outputs the characteristic value based on the last measurement result and obtained by the operation unit 27a.

The storage unit 28 stores an optical measurement program that causes the optical measurement apparatus 1 to perform an optical measurement process and stores various types of information on the optical measurement process. The storage unit 28 stores measurement results that the determination unit 27c has determined to be adopted and stores characteristic values obtained by the operation unit 27a by performing operations.

The external communication unit 29 is configured using a communication interface. The external communication unit 29 receives information on the optical measurement process from an external device to which the external communication unit 29 is connected and with which it communicates via the Internet or the like and transmits various types of data containing measurement results and operation results.

The probe 3 is implemented using one or more optical fibers. For example, the probe 3 includes an irradiation fiber that guides light, which is supplied from the light source, and that emits the light to the measurement target; and a light receiving fiber on which the light returned from the measurement target is incident. When the LEBS technology is used, multiple light receiving fibers are used to receive at least two scattering lights with different scattering angles. The probe 3 includes a proximal end portion 31 that is detachably connected to the connector 23 of the main body device 2, a flexible portion 32 that has flexibility, and a distal end 33 from which light supplied from the light source unit 22 is emitted and on which the scattering light from the measurement target is incident.

The optical measurement apparatus 1 is combined with, for example, an endoscope system to observe internal organs, such as digestive organs.

Figure 2:
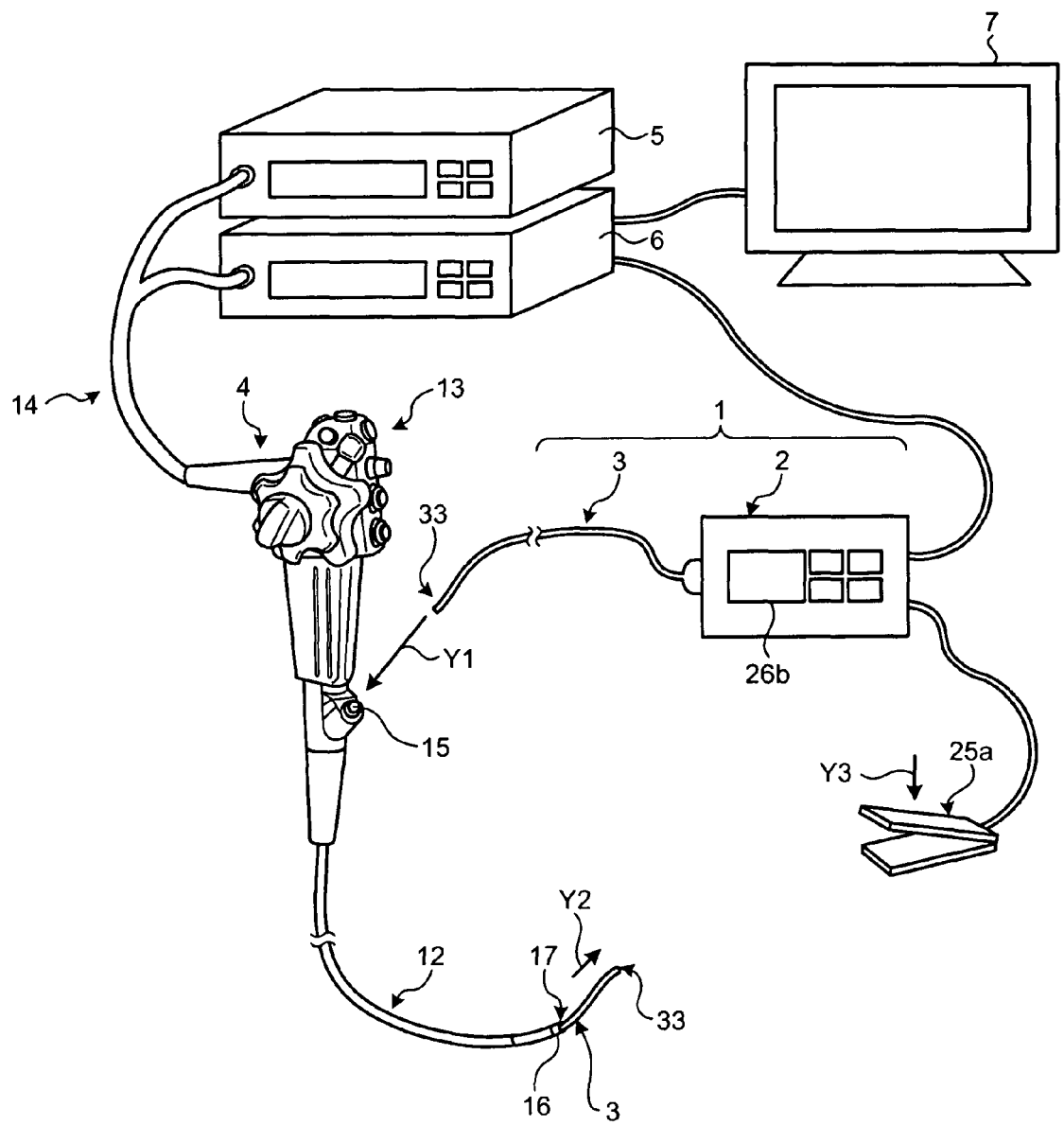
FIG. 2 is a diagram illustrating a configuration of a microscope system and the attachment of a probe to an optical measurement apparatus.

FIG. 2 is a diagram illustrating the configuration of the microscope system and attachment of the probe 3 in the optical measurement apparatus 1. In FIG. 2, a flexible universal cord 14 that extends from a side portion of an operation unit 13 is connected to a light source device 5 and to a signal processing device 6 that processes a subject image captured at a distal end portion 16 of an endoscope 4. The signal processing device 6 is connected to a display 7. The display 7 displays various types of information on an examination including subject images processed by the signal processing device 6.

The probe 3 is inserted, as indicated by the arrow Y1, from a probe channel insertion port 15 near the external operation unit 13 of the endoscope 4, which is inserted into the subject. As indicated by the arrow Y2, the distal end 33 of the probe 3 protrudes, via an insertion unit 12, from an opening 17 of the distal end portion 16 connected to the probe channel. Accordingly, the probe 3 is inserted into the subject and starts optical measurement.

A display screen 26b that displays and outputs a result of evaluation performed by the validity evaluator 27b and a characteristic value obtained by the operation unit 27a by performing an operation is provided on a predetermined surface of the main body device 2. The main body device 2 includes a foot switch device 25a that constitutes a part of the input unit 25. Upon being pushed as represented by the arrow Y3, the foot switch device 25a inputs instruction information containing an instruction to adopt the measurement result to the controller 27. The main body device 2 of the optical measurement apparatus 1 and the signal processing device 6 are connected to each other and various types of information processed by the optical measurement apparatus 1 are output to the signal processing device 6.

Figure 3:
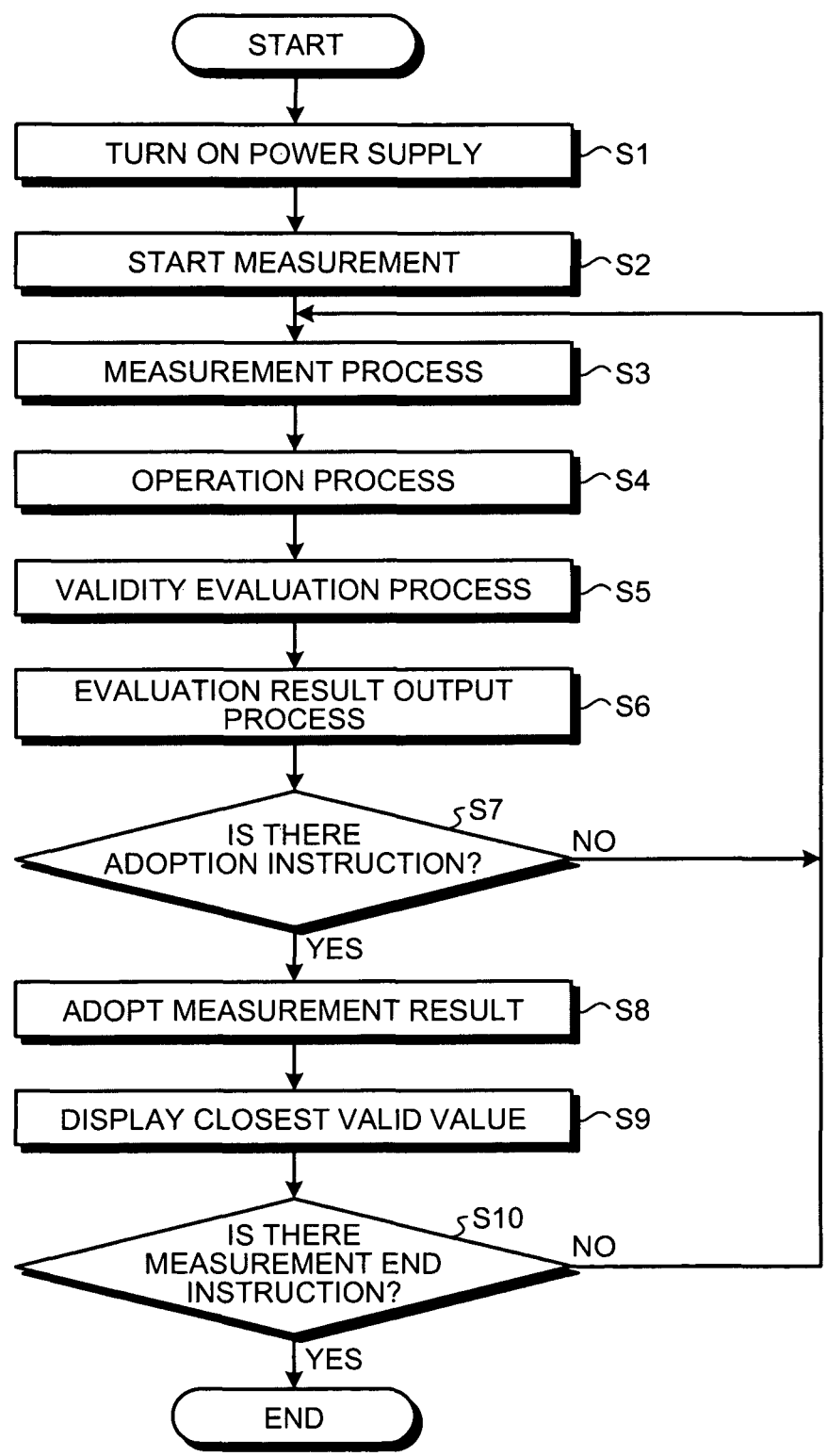
FIG. 3 is a flowchart of a procedure of an optical measurement process performed by the optical measurement apparatus in FIG. 1.

The optical measurement process performed by the optical measurement apparatus 1 according to the present embodiment will be described. FIG. 3 is a flowchart of a procedure of the optical measurement process performed by the optical measurement apparatus 1 in FIG. 1.

According to a user's operation of the optical measurement apparatus 1, the power supply of the optical measurement apparatus 1 is turned on (step S1), and the optical measurement apparatus 1 moves on to a sequential measurement mode, where it starts sequential measurements (step S2). A series of initial setting processes including a white balance adjustment data obtaining process may be performed between the power-on and the start of sequential measurements.

The light source unit 22 then performs a light emission process to irradiate a living tissue with light from the proximal end of the probe 3 and the measurement unit 24 performs a measurement process to measure the light returned from the living tissue and output from the probe 3 (step S3). The result of the measurement performed by the measurement unit 24 is a signal waveform representing an intensity distribution in a predetermined wavelength range of returned light with multiple angles.

The operation unit 27a performs an operation process where it obtains a characteristic value of the living tissue by performing multiple types of operation processes on the basis of the result of the measurement performed by the measurement unit 24 (step S4). For example, the operation unit 27a obtains, as a characteristic value, the amount of hemoglobin, the size of a cell nucleus, or the amount of chromatin.

The validity evaluator 27b performs a validity evaluation process to evaluate whether the characteristic value obtained by the operation unit 27a is valid (step S5).

The output unit 26 performs an evaluation result output process to output the result of the evaluation performed by the validity evaluator 27b (step S6). For example, when the evaluation result indicates that the characteristic value is valid, the display unit 26a lights up a validity area 26c of the display screen 26b of the main body device 2 by using green light. When the evaluation result indicates that the characteristic value is invalid, the display unit 26a turns off the lighting of the validity area 26c.

According to instruction information input from the input unit 25, the determination unit 27c determines whether there is an instruction to adopt a result of measurement performed by the measurement unit 24 (step S7).

When the determination unit 27c determines that there is no instruction to adopt the measurement result (NO at step S7), the determination unit 27c does not adopt this measurement result, goes to step S3, and causes the light source unit 22 and the measurement unit 24 to perform the next measurement process. In this case, the measurement result, which is not adopted, and the characteristic value, which is obtained on the basis of the measurement result, are temporarily stored in a memory (not shown) in the controller 27 and deleted, for example, after a predetermined time elapses.

In contrast, when the determination unit 27c determines that there is an instruction to adopt the measurement result (YES at step S7), the determination unit 27c adopts the result of the measurement performed by the measurement unit 24 regardless of the result of the validity evaluation performed by the validity evaluator 27b (step S8). In this case, the adopted measurement result is stored together with the obtained characteristic value in the storage unit 28.

The determination unit 27c causes the display unit 26a to display the characteristic value obtained by the operation unit 27a by performing an operation on the basis of the measurement result that is the last measurement result determined to be adopted out of measurement results that are evaluated to be valid by the validity evaluator 27b, i.e., to display the last valid value (step S9).

Figure 4:
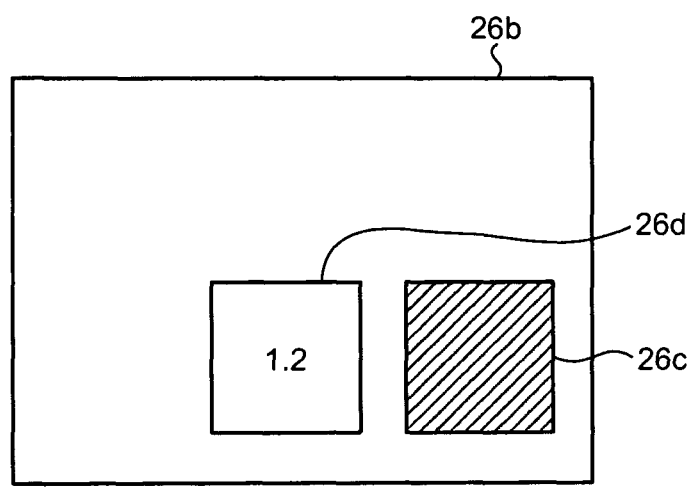
FIG. 4 is a diagram of an example of a display screen in FIG. 2.
Figure 5:
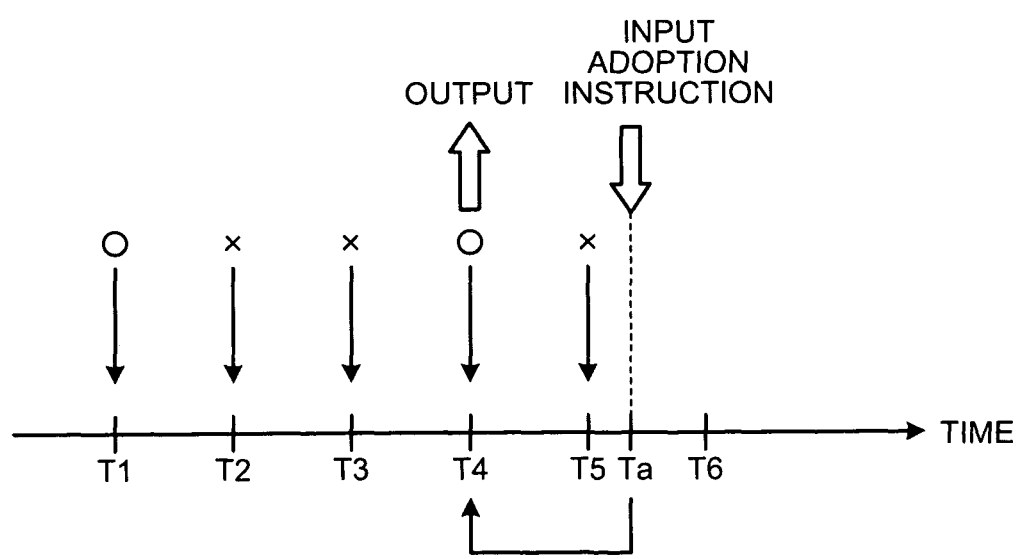
FIG. 5 is a diagram illustrating the process details at step S8 and step S9 in FIG. 3.

A specific description is here provided with reference to FIG. 5. FIG. 5 shows an example in which the optical measurement apparatus 1 performs a measurement process at timing of times T1 to T6. The results of the measurements at the times T1 and T4 are evaluated as valid, and the results of the measurements at the times T2, T3, and T5 are evaluated to be invalid. In this case, when the input unit 25 inputs instruction information of an adoption instruction at a time Ta (T5<Ta<T6), a characteristic value is output that is obtained by performing an operation on the basis of the result of the measurement at the time T4 that is the closest to the time Ta out of the results of the measurements at the times T1 and T4 that are measurement results obtained before the time Ta and determined to be valid by the validity evaluator 27b. For example, as shown in FIG. 4, the display unit 26a displays, on a characteristic value display area 26d of the display screen 26b, the valid characteristic value (for example, the amount of hemoglobin) that is the last measurement result determined to be adopted.

Thereafter, on the basis of the instruction information from the input unit 25, the controller 27 determines whether there is an instruction to end measurement (step S10). When the controller 27 determines that there is no instruction to end measurement (NO at step S10), the controller 27 goes to step S3 and causes the light source unit 22 and the measurement unit 24 to perform the next measurement process.

In contrast, when the controller 27 determines there is an instruction to end measurement (YES at step S10), the controller 27 controls operations of each component and ends the measurement process.

Figure 6:
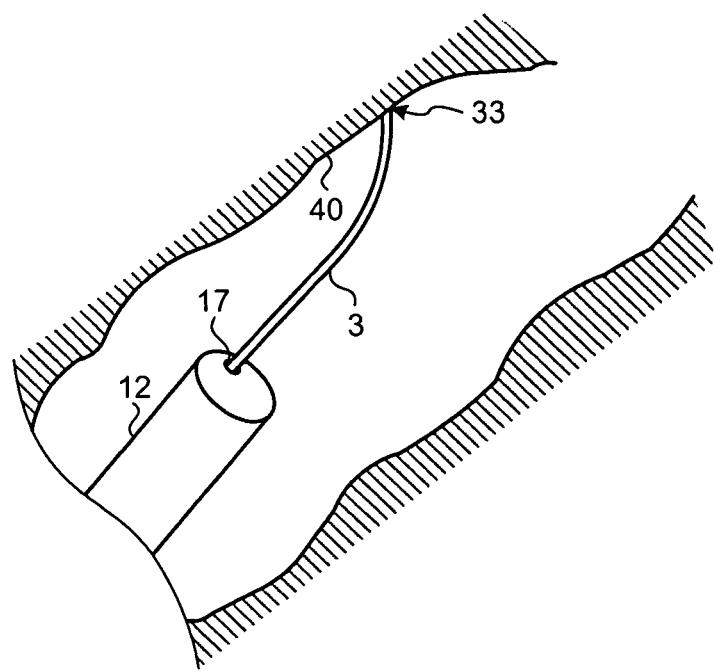
FIG. 6 is a diagram illustrating the measurement conditions under which the optical measurement apparatus in FIG. 2 performs.
Figure 7:
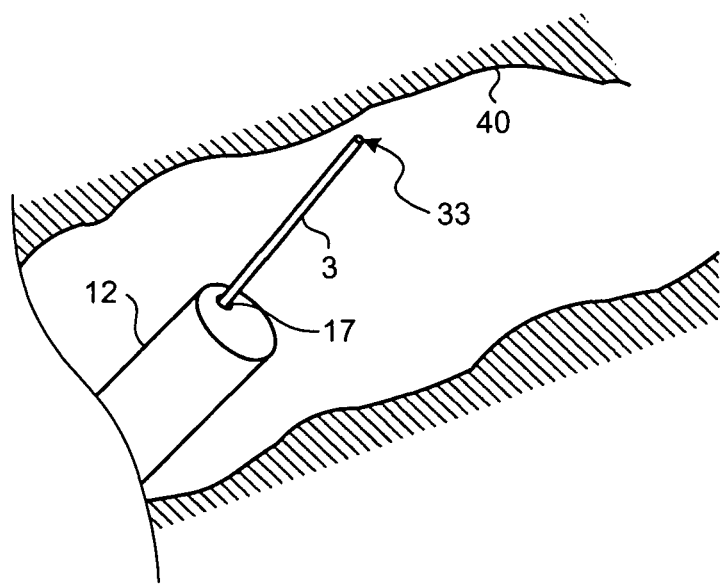
FIG. 7 is a diagram illustrating the measurement conditions under which the optical measurement apparatus in FIG. 2 performs.

In the optical measurement apparatus 1, as shown in FIG. 6, the distal end 33 of the probe 3 protruding from the opening 17 at the distal end of the insertion unit 12 of the endoscope brings into contact with the surface of a living tissue 40 in the lumen organs, which allows stable measurement and thus a valid measurement result can often be obtained. In contrast, when the distal end 33 of the probe 3 cannot be stably fixed to the living tissue 40 due to peristalsis of the internal organs, a valid measurement result often cannot be obtained. In general, due to movement from pulsation or peristalsis, it is often difficult to fix the distal end 33 of the probe 3 at the measurement position on the living tissue when a measurement is performed on internal organs, such as the digestive organs. Furthermore, the observation light of the endoscope during measurement may become interfering stray light, which makes it difficult to accurately measure the light returned from the living tissue.

As described above, the optical measurement apparatus cannot necessarily obtain a valid measurement result. Furthermore, in order to avoid re-examination, the operator often confirms whether a valid measurement result is obtained while performing measurement. However, the result obtained by the optical measurement apparatus 1 is an image obtained by an endoscope about which it can be determined by visual check whether there is an error but a signal wave indicating the intensity distribution of the returned light with multiple angles or numerical data indicating a characteristic value. Thus, it is difficult for the operator to determine whether the obtained measurement result and the operation result are valid by only checking a signal waveform or numerical data. Accordingly, determining the validity of the measurement result and the operation result during the measurement is the workload of the user.

In this embodiment, when optical measurement is performed on a living tissue, the validity of a characteristic value obtained by an operation process in each measurement process is evaluated and the result of the evaluation is output so that the operator is informed of whether a valid measurement result is obtained.

By confirming the evaluation result, the operator can know easily whether valid data is obtained and can continue the measurement process while knowing the validity of the measurement result. In other words, by only checking the result of evaluation on the measurement result output from the optical measurement apparatus 1, the operator can, without analyzing the signal waveform, check whether the obtained measurement result is a result observation of an item that the operator desires. Thus, when the operator determines, on the basis of the evaluation result, that the measurement result of the desired item is obtained, the operator can efficiently obtains the result of measurement of the desired item and the characteristic value by only selecting adoption of the measurement result. Thus, it is unnecessary to repeat measurements in the same position until the result of the measurement of the desired item is obtained.

Thus, according to the present embodiment, the workload on the operator to select a valid measurement result can be reduced, which makes the process to obtain the result of measurement of the item desired by the operator efficient.

Furthermore, in the present embodiment, regardless of the result of evaluation performed by the validity evaluator 27b, priority is given to the adoption instruction from the operator and thus only the measurement result and characteristic value for which an adoption instruction is given are stored. Accordingly, for example, when invalid measurement results are stored and analyzed, the operator can flexibly select, out of sequential multiple measurement results, only a measurement result that meets the demand as in the case in which invalid measurement results are stored and analyzed.

Steps S3 to S7 or steps S3 to S10 are performed repeatedly corresponding to a measurement interval that is set by the operator. If it is expected that there is strenuous movement of the internal organ that is the measurement target, the measurement interval may be set short, for example, to be equal to or less than 100 milliseconds. If it is expected that there is no movement of the internal organ that is the measurement target, the measurement interval may be set long, for example, to more than 100 milliseconds. Alternatively, the measurement interval may be varied according to the result of an evaluation performed by the validity evaluator 27b. For example, when the distal end 33 of the probe 3 is outside the subject or when the result of an evaluation performed by the validity evaluator 27b indicates that the characteristic value is invalid, the measurement interval may be set long. Because the validity of the operation result increases as the distal end 33 of the probe 3 approaches the living tissue, the measurement interval may be set short according to the increase in the validity.

Figure 8:
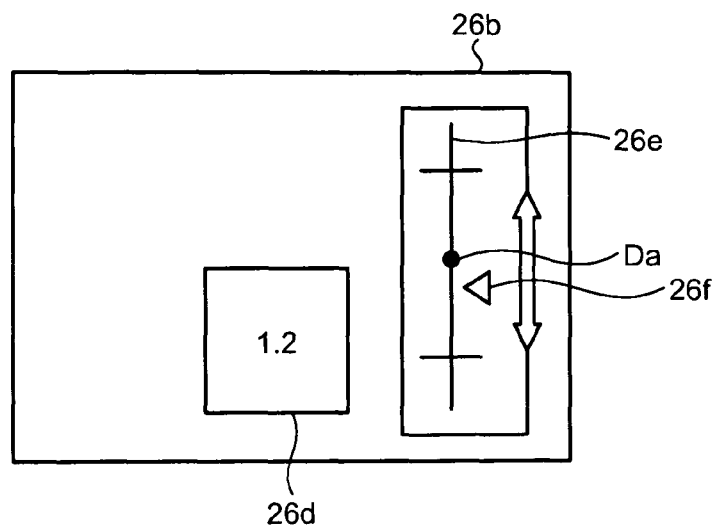
FIG. 8 is a diagram of another example of the display screen in FIG. 2.

In the present embodiment, the case in which the result of evaluation of the validity of the measurement result is displayed on the validity area 26c is described as an example. However, this is not a limitation. For example, as shown in FIG. 8, an evaluation bar 26e containing an acceptable range of characteristic values that can be evaluated to be valid and a slider 26f movable, as the arrow represents, along the evaluation bar 26e may be displayed on the display screen 26b and it may be indicated, with the slider 26f, where a characteristic value obtained by the operation unit 27a by performing an operation is on the evaluation bar 26e. The evaluation bar 26e also represents an average value Da of characteristic values that are evaluated to be valid.

Figure 9:
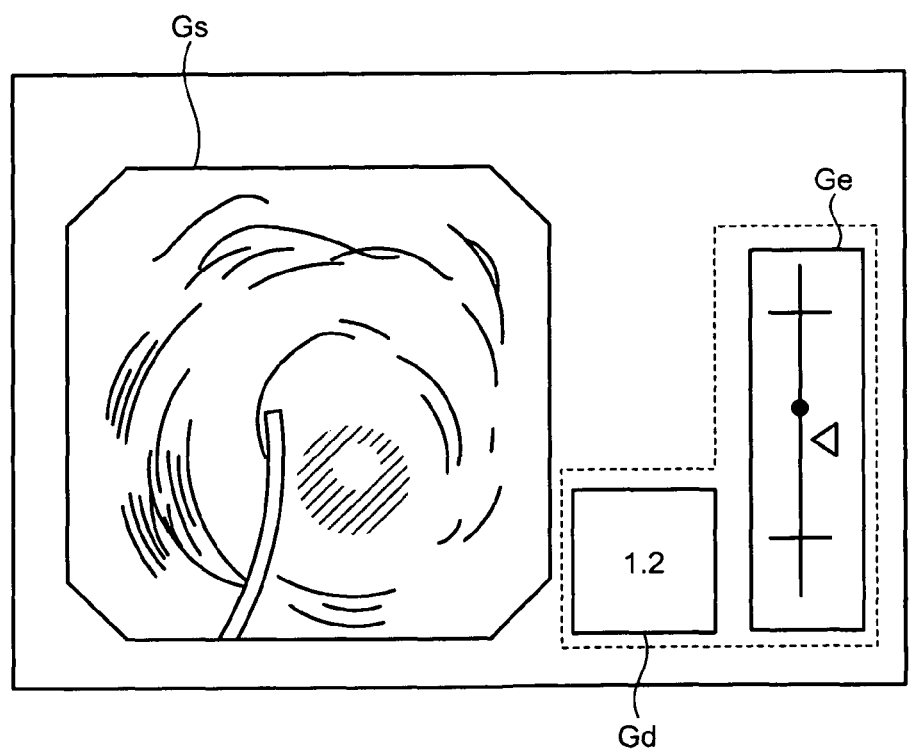
FIG. 9 is a diagram of an example of the display screen of the display in FIG. 2.

The display 7 displays and outputs the evaluation result and the last valid value. As shown in FIG. 9, the display 7 displays and outputs, together with an in-vivo image Gs captured by the endoscope 4, an evaluation bar image Ge indicating the result of evaluation performed by the validity evaluator 27b. The display 7 displays and outputs, together with the in-vivo image Gs and the evaluation bar image Ge, a characteristic value image Gd that indicates the last valid value determined to be adopted.

In the present embodiment, the case in which the result of evaluating validity of the measurement result is displayed and output is described as an example. However, this is not a limitation. For example, the optical measurement apparatus 1 may output, from the speaker, audio information in which the frequency is varied according to the evaluation result.

(First Modification)

In a first modification, when adopting a measurement result, priority is given to the result of evaluation performed by the validity evaluator 27b.

Figure 10:
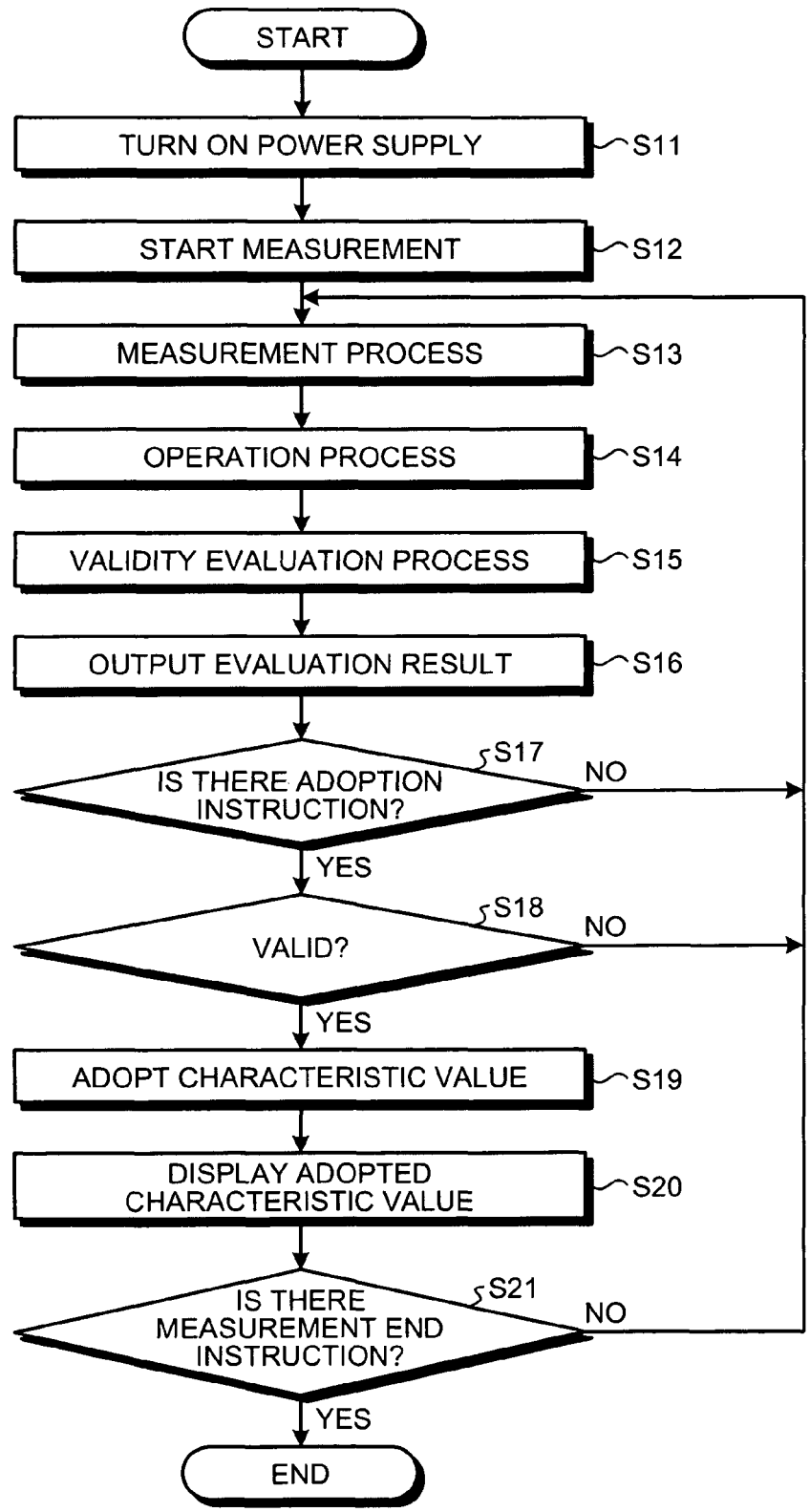
FIG. 10 is a flowchart of a procedure of an optical measurement process of a first modification of the optical measurement apparatus in FIG. 2.

FIG. 10 is a flowchart of a procedure of an optical measurement process of the first modification of the optical measurement apparatus 1.

In the first modification, as shown in FIG. 10, as in the case of steps S1 to S7 in FIG. 3, after the power supply of the optical measurement apparatus 1 is turned on (step S11), the optical measurement apparatus 1 starts sequential measurements (step S12) and performs a measurement process (step S13), an operation process (step S14), a validity evaluation process (step S15), an evaluation result output process (step S16), and a process to determine whether there is an instruction to adopt the measurement result (step S17). When the determination unit 27c determines that there is no instruction to adopt the measurement result (NO at step S17), the determination unit 27c does not adopt the measurement result and the characteristic value as in the case of the above-described embodiment, goes to step S13, and causes the light source unit 22 and the measurement unit 24 to perform the next measurement process.

In contrast, when the determination unit 27c determines that there is an instruction to adopt the measurement result (YES at step S17), the determination unit 27c determines whether the evaluation performed by the validity evaluator 27b on the characteristic value indicates validity (step S18).

When the determination unit 27c determines that the evaluation on the characteristic value indicates invalidity (NO at step S18), the determination unit 27c does not adopt the result of the measurement performed by the measurement unit 24, goes to step S13, and causes the light source unit 22 and the measurement unit 24 to perform the next measurement process.

In contrast, when the determination unit 27c determines that the evaluation on the characteristic value indicates validity (YES at step S18), the determination unit 27c adopts the characteristic value and the measurement result (step S19) and causes the display unit 26a to display the adopted characteristic value (step S20).

As in the case of step S10 in FIG. 3, the controller 27 then determines whether there is an instruction to end measurement (step S21). When the controller 27 determines that there is no instruction to end measurement (NO at step S21), the controller 27 goes to step S13 and causes the light source unit 22 and the measurement unit 24 to perform the next measurement process. In contrast, when the controller 27 determines that there is an instruction to end measurement (YES at step S21), the controller 27 controls operations of each component and ends the measurement process.

As described above, in the first modification, even if the operator gives an adoption instruction, the characteristic value and the measurement result are not adopted when the evaluation performed by the validity evaluator 27b indicates invalidity. In other words, in the first modification, the measurement result and the characteristic value are adopted only when the operator issues an adoption instruction and the validity evaluator 27b determines that the characteristic value is valid; therefore, and thus only accurate valid data can be obtained.

(Second Modification)

In a second modification, adoption of a characteristic value and the like is accepted only when the result of evaluation performed by the validity evaluator 27b indicates validity.

Figure 11:
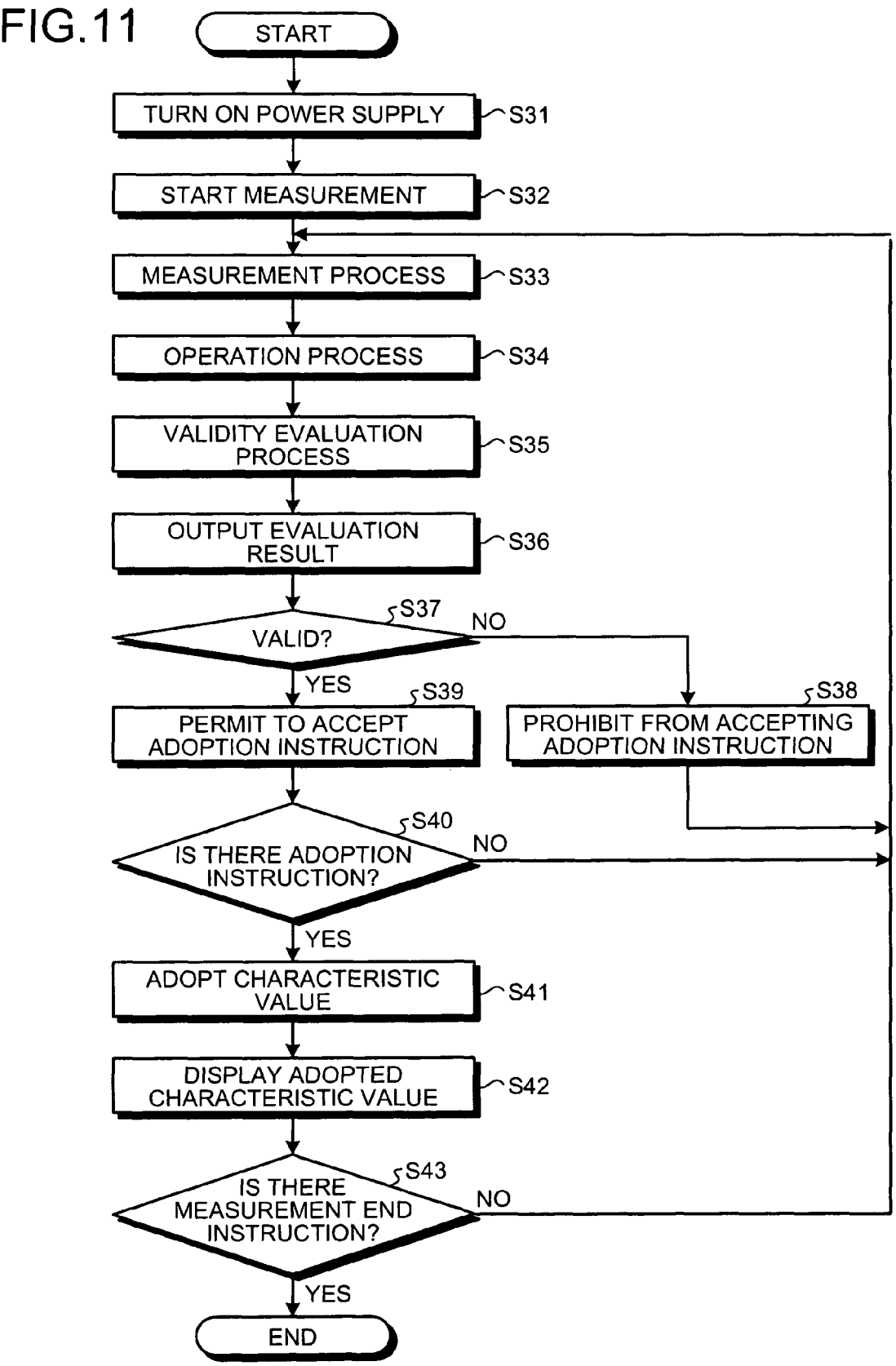
FIG. 11 is a flowchart of a procedure of an optical measurement process of a second modification of the optical measurement apparatus in FIG. 2.

FIG. 11 is a flowchart of a procedure of an optical measurement process of the second modification of the optical measurement apparatus 1.

The processes performed at steps S31 to S36 in FIG. 11 are the same as those performed at steps S1 to S6 in FIG. 3, respectively.

The determination unit 27c then determines whether the evaluation performed by the validity evaluator 27b on the operation result (characteristic value) indicates validity (step S37).

When the determination unit 27c determines that the evaluation on the characteristic value indicates invalidity (NO at step S37), the determination unit 27c prohibits the input unit 25 from accepting instruction information of an instruction to adopt the measurement result (step S38). Accordingly, even when the foot switch device 25a is operated, the input unit 25 does not accept instruction information of an instruction to adopt the measurement result. The determination unit 27c then goes to step S33 and causes the light source unit 22 and the measurement unit 24 to perform the next measurement process.

In contrast, when the determination unit 27c determines that the evaluation on the characteristic value indicates validity (YES at step S37), the determination unit 27c permits the input unit 25 to accept instruction information of an instruction to adopt the measurement result (step S39). In response to the permission, the determination unit 27c determines, on the basis of instruction information input from the input unit 25, whether there is an instruction to adopt the measurement result (step S40).

When the determination unit 27c determines there is no instruction to adopt the measurement result (NO at step S40), the determination unit 27c goes to step S44 and causes the light source unit 22 and the measurement unit 24 to perform the next measurement process. In contrast, when the determination unit 27c determines there is an instruction to adopt the measurement result (YES at step S40), the determination unit 27c adopts the measurement result and the characteristic value (step S41) and causes the display unit 26a to display the adopted characteristic value (step S42).

As in the case of step S10 in FIG. 3, the controller 27 then determines whether there is an instruction to end measurement (step S43). When the controller 27 determines that there is no instruction to end measurement (NO at step S43), the controller 27 goes to step S33 and causes the light source unit 22 and the measurement unit 24 to perform the next measurement process. In contrast, when the controller 27 determines that there is an instruction to end measurement (YES at step S43), the controller 27 controls operations of each component and ends the measurement process.

As described, in the second modification, an instruction to adopt a characteristic value and a measurement result are accepted only when the evaluation performed by the validity evaluator 27b indicates validity. This is so that the validity evaluator 27b adopts only the measurement result and characteristic value that are evaluated to be valid; therefore, only accurate valid data can be obtained.

(Third Modification)

In a third modification, the validity evaluator 27b does not perform validity evaluation by obtaining a characteristic value to be finally obtained but evaluates, on the basis of the operation result in the middle of the operation to obtain a characteristic value performed by the operation unit 27a, whether the result of measurement performed by the measurement unit 24 is valid.

Figure 12:
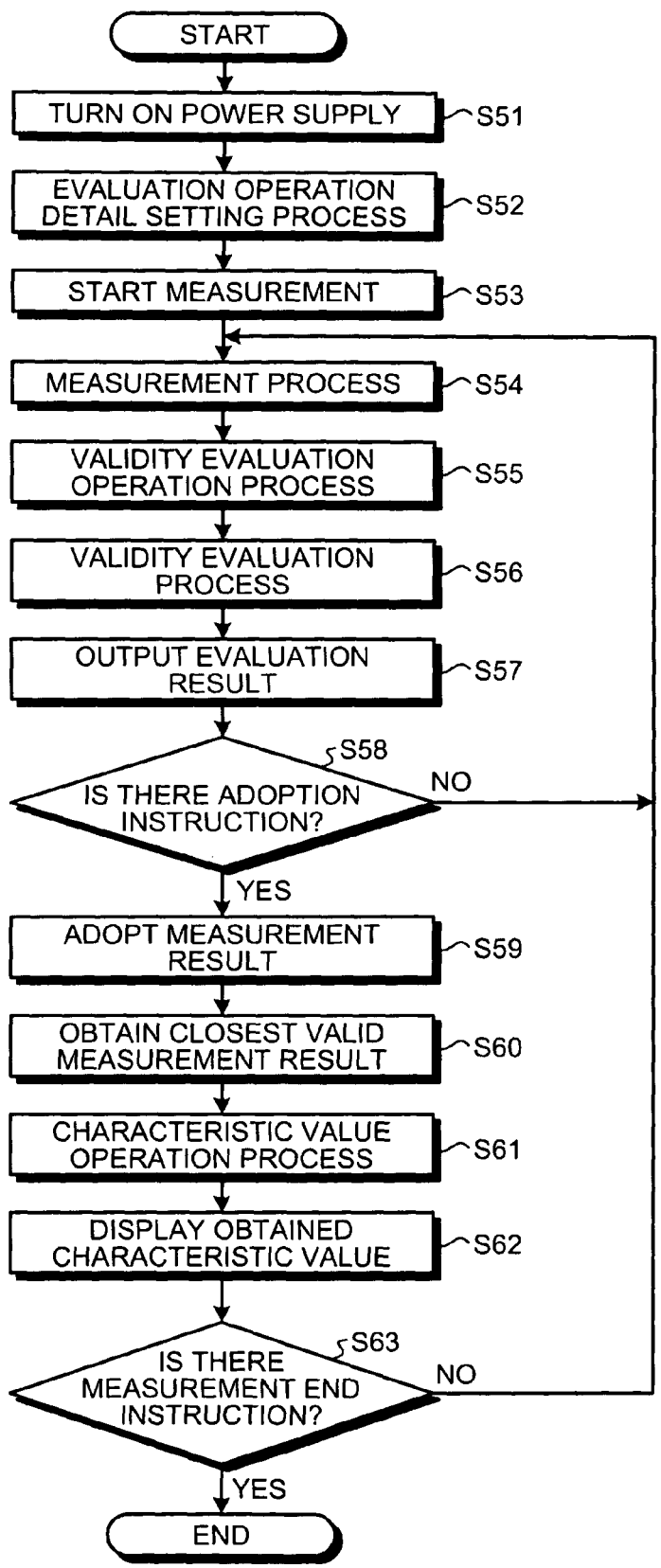
FIG. 12 is a flowchart of a procedure of an optical measurement process of a third modification of the optical measurement apparatus in FIG. 2.

FIG. 12 is a flowchart of a procedure of an optical measurement process of the third modification of the optical measurement apparatus 1.

As shown in FIG. 12, after the power supply of the optical measurement apparatus 1 is turned on (step S51), as in the case of step S1 in FIG. 3, according to an operator's operation on the input unit 25, an evaluation operation detail setting process is performed to set the operation details of the evaluation operation process to obtain an operation result for validity evaluation (step S52).

As in the case of steps S2 and S3 in FIG. 3, sequential measurements are started (step S53) and a measurement process is performed (step S54). Thereafter, the operation unit 27a performs, with respect to the obtained measurement result, a validity evaluation operation process to perform the operation process that is set at the evaluation operation detail setting process (step S55).

For example, an operation process to obtain the value of the integral of the reflectance of returned light, the slope of a signal waveform, the frequency of the waveform, and the intensity ratio between two predetermined wavelengths are taken as the validity evaluation operation process. As described above, the operation unit 27a does not perform an operation process to obtain a characteristic value, which is set as one to be finally obtained, but performs an operation process up to the middle of the operation process to obtain a characteristic value and then outputs the result of the operation (intermediate value) to the validity evaluator 27b.

The validity evaluator 27b then performs a validity evaluation process to evaluate whether the result of the operation (intermediate value) performed by the operation unit 27a is valid (step S56). For example, a sufficient reflectance cannot be obtained when the distal end 33 of the probe 3 is outside the living subject, or when the distal end 33 of the probe 3 does not sufficiently make contact with the living tissue. Thus, when the operation unit 27a calculates the value of the integral of the reflectance of the returned light as the validity evaluation operation process, the validity evaluator 27b evaluates whether the result of the measurement performed by the measurement unit 24 is valid by comparing the value of the integral with a threshold, which is set beforehand on the basis of the value of the integral of the reflectance of the returned light obtained when the measurement is valid, or within an acceptable range. It is satisfactory if the operator sets, on the basis of not only the spectral reflectance but the measurement principle employed by the optical measurement apparatus 1, the operation details of the validity evaluation operation process and the threshold or the acceptable range of the validity evaluation process.

As in the case of step S6, the output unit 26 performs an evaluation result output process to output the result of the evaluation performed by the validity evaluator 27b (step S57).

The determination unit 27c then determines, according to whether instruction information is input from the input unit 25, whether there is an instruction to adopt the measurement result (step S58).

When the determination unit 27c determines that there is no instruction to adopt the measurement result (NO at step S58), the determination unit 27c goes to step S54 and causes the light source unit 22 and the measurement unit 24 to perform the next measurement process.

In contrast, when the determination unit 27c determines that there is an instruction to adopt the measurement result (YES at step S58), the determination unit 27c adopts the measurement result (step S59) and obtains the measurement result that is the last measurement result determined to be adopted out of measurement results evaluated to be valid by the validity evaluator 27b (step S60). The operation unit 27a then performs, by using the obtained valid measurement result, a characteristic value operation process to obtain a characteristic value to be finally obtained (step S61) and causes the display unit 26a to display the obtained characteristic value (step S62). In other words, the operation unit 27a performs the operation process to obtain a characteristic value to be finally obtained only with respect to the valid measurement result that is the last measurement result determined to be adopted.

As in the case of step S10 in FIG. 3, the controller 27 then determines whether there is an instruction to end measurement (step S63). When the controller 27 determines that there is no instruction for ending measurement (NO at step S63), the controller 27 goes to step S54 and causes the light source unit 22 and the measurement unit 24 to perform the next measurement process. In contrast, when the controller 27 determines that there is an instruction to end measurement (YES at step S63), the controller 27 controls operations of each component and ends the measurement process.

As described above, in the third modification, validity is not evaluated by obtaining a characteristic value, which is to be finally obtained, by performing an operation in each measurement process, but validity is evaluated on the basis of the operation result (intermediate value) in the middle of the operation process to obtain a characteristic value. Thus, in the third modification, it is not required to perform a complicated operation process to evaluate validity.

Furthermore, in the third modification, the operation process to obtain a characteristic value to be finally obtained is performed only on the valid measurement result that is the last measurement result that is evaluated as valid by the validity evaluator 27b and for which an adoption instruction is given.

Accordingly, in the third modification, even if the measurement interval cannot be set long due to a limitation of the processing performance of the operation unit 27a, evaluation of the validity of the measurement result and obtaining of a characteristic value can be performed appropriately and efficiently.

(Fourth Modification)

In a fourth modification, when adopting a measurement result, priority is given to the result of evaluation of an intermediate value performed by the validity evaluator 27b.

Figure 13:
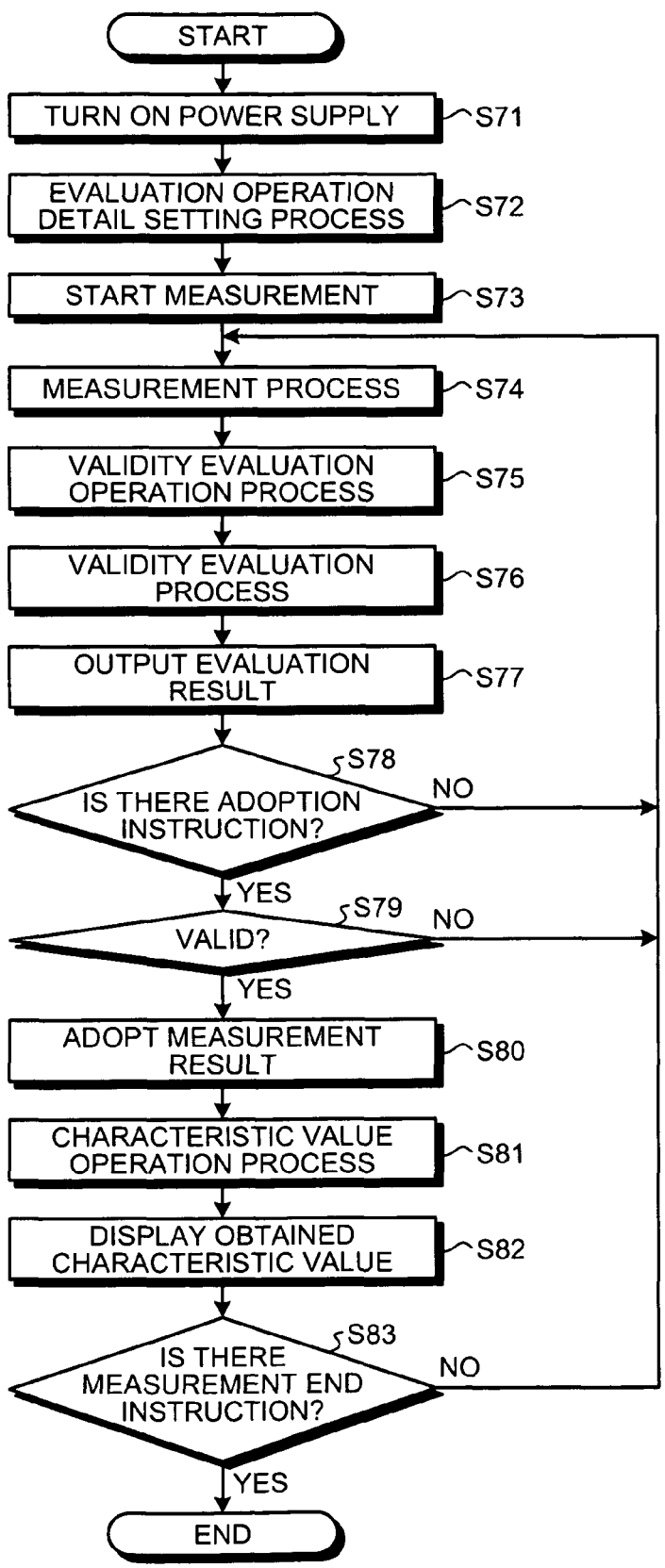
FIG. 13 is a flowchart of a procedure of an optical measurement process of a fourth modification of the optical measurement apparatus in FIG. 2.

FIG. 13 is a flowchart of a procedure of an optical measurement process of the fourth modification of the optical measurement apparatus 1.

Steps S71 to S78 in FIG. 13 are the same as steps S51 to S58 in FIG. 12.

At step S78, when the determination unit 27c determines that there is an instruction to adopt the measurement result (YES at step S78), the determination unit 27c determines whether the evaluation performed by the validity evaluator 27b on the measurement result indicates validity (step S79).

When the determination unit 27c determines that the evaluation on the measurement result indicates validity (NO at step S79), the determination unit 27c does not adopt the measurement result, goes to step S74, and causes the light source unit 22 and the measurement unit 24 to perform the next measurement process.

In contrast, when the determination unit 27c determines that the evaluation on the measurement result indicates validity (YES at step S79), the determination unit 27c adopts the measurement result (step S80) and an adoption instruction is given. In addition, on the basis of the measurement result evaluated to be valid, the determination unit 27c performs a characteristic value operation process to obtain a characteristic value to be finally obtained (step S81) and causes the display unit 26a to display the obtained characteristic value (step S82).

As in the case of step S63 in FIG. 12, the controller 27 then determines whether there is an instruction to end measurement (step S83). When the controller 27 determines that there is no instruction to end measurement (NO at step S83), the controller 27 goes to step S74 and causes the light source unit 22 and the measurement unit 24 to perform the next measurement process. In contrast, when the controller 27 determines that there is an instruction to end measurement (YES at step S83), the controller 27 controls operations of each component and ends the measurement process.

As described above, in the fourth modification, only a measurement result for which the operator gives an adoption instruction and that is evaluated to be valid by the validity evaluator 27b is adopted and a characteristic value is obtained by performing an operation only on the adopted measurement result; therefore, only valid data can be obtained accurately and efficiently.

(Fifth Modification)

In a fifth modification, the adoption of a measurement result is only accepted when the result of evaluation performed by the validity evaluator 27b on the intermediate value is valid.

Figure 14:
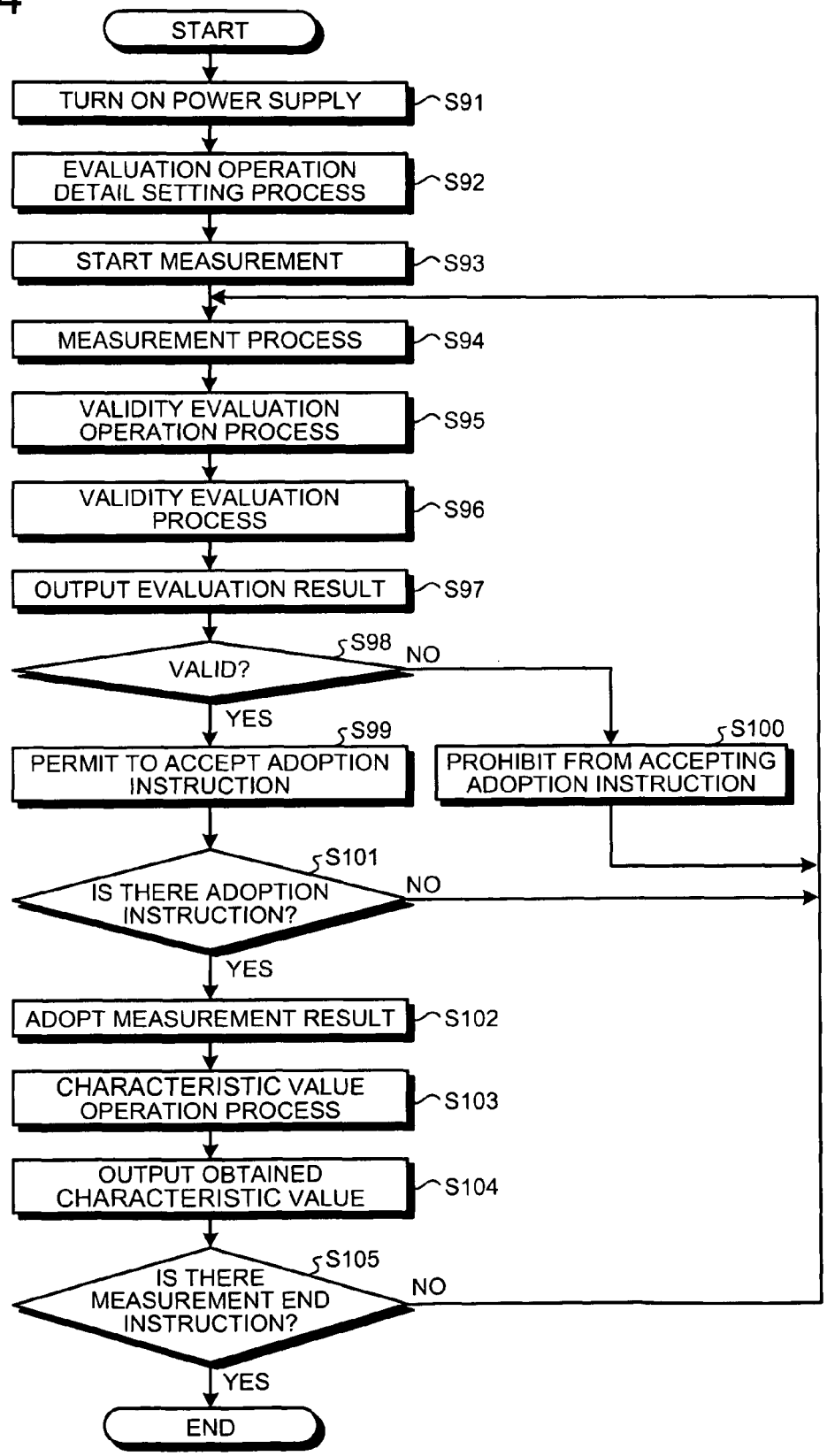
FIG. 14 is a flowchart of a procedure of an optical measurement process of a fifth modification of the optical measurement apparatus in FIG. 2.

FIG. 14 is a flowchart of a procedure of optical measurement process of the fifth modification of the optical measurement apparatus 1.

Steps S91 to S97 in FIG. 14 are the same as steps S51 to S57 in FIG. 12.

The determination unit 27c determines whether the evaluation performed by the validity evaluator 27b on the measurement result indicates validity (step S98).

When the determination unit 27c determines that the evaluation of the measurement result indicates invalidity (NO at step S98), the determination unit 27c prohibits the input unit 25 from accepting instruction information of an instruction to adopt the measurement result (step S100). The determination unit 27c then goes to step S94 and causes the light source unit 22 and the measurement unit 24 to perform the next measurement process.

In contrast, when the determination unit 27c determines that the evaluation on the measurement result indicates validity (YES at step S98), the determination unit 27c permits the input unit 25 to accept instruction information of an instruction to adopt the measurement result (step S99). In response to the permission, the determination unit 27c determines, on the basis of instruction information input from the input unit 25, whether there is an instruction to adopt the measurement result (step S101).

When the determination unit 27c determines that there is no instruction to adopt the measurement result (NO at step S101), the determination unit 27c does not adopt the measurement result, goes to step S94, and causes the light source unit 22 and the measurement unit 24 to perform the next measurement process.

In contrast, when the determination unit 27c determines that there is an instruction to adopt the measurement result (YES at step S101), the determination unit 27c adopts the measurement result (step S102). On the basis of the measurement result, the determination unit 27c performs a characteristic value operation process to obtain a characteristic value to be finally obtained (step S103) and causes the display unit 26a to display the obtained characteristic value (step S104).

As in the case of step S63, the controller 27 then determines whether there is an instruction to end measurement (step S105). When the controller 27 determines that there no any instruction to end measurement (NO at step S105), the controller 27 goes to step S94 and causes the light source unit 22 and the measurement unit 24 to perform the next measurement process. In contrast, when the controller 27 determines that there is an instruction to end measurement (YES at step S105), the controller 27 controls operations of each component and ends the measurement process.

As described above, in the fifth modification, an instruction to adopt the measurement result is accepted only when the evaluation performed by the validity evaluator 27b indicates validity and only the measurement result that is evaluated to be valid by the validity evaluator 27b can be adopted. Furthermore, in the fifth modification, a characteristic value is obtained by performing an operation only with respect to the measurement result for which an adoption instruction is given; therefore, only valid data can be obtained accurately and efficiently.

In the optical measurement apparatus 1, multiple modes in which the optical measurement process of the first to fifth modifications can be each performed are set as processing modes of the optical measurement process. Thus, by setting, out of the multiple modes, a mode in which the desired optical measurement process is performed, the operator can flexibly select a measurement result obtaining method and a characteristic value obtaining method.

Alternatively, as a method of evaluating validity of a characteristic value, validity of a characteristic value may be evaluated by storing beforehand, with respect to a population of a combination of a normal group and a disease group of living tissue, an average and a standard deviation of the characteristic value and by knowing the position of the characteristic value, which is obtained from the measured value by performing an operation, in the population distribution (for example, it is determined whether the position is within a 95% confidence interval of the population average).

The above-described embodiment is implemented by executing a prepared optical measurement program on a computer system. In the present embodiment, the apparatus for optical measurement of a living tissue is implemented by reading and executing the optical measurement program that is recorded in a predetermined recording medium. Here, the predetermined recording medium includes various media: "portable physical media", such as a flexible disk, a CD-ROM, a MO disk, a DVD disk, a magnetic optical disk, and an IC card; "fixed physical media", such as a hard disk drive, RAM, and RAM that is installed in and outside a computer system; or a "communication media", such as a public line connected via a modem or a LAN/WAN to which other computer systems and a server is connected and which are media that store a program for a short period when the program is transmitted.

Additional advantages and modifications will readily occur to those skilled in the art; therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical measurement apparatus for measuring an optical characteristic of a living tissue, the optical measurement apparatus comprising:
    a light source configured to emit irradiation light to be emitted to the living tissue;
    a spectrometer configured to measure at least one of reflection light and scattering light from the living tissue;
    a controller configured to perform a validity evaluation operation process on the basis of results of the measurement performed by the spectrometer, and to evaluate, on the basis of an operation result for validity evaluation, whether the results of the measurement performed by the spectrometer are valid;
    an output processor configured to output at least a result of the evaluation performed by the controller; and
    a switch configured to input instruction information containing an instruction to adopt the results of the measurement performed by the spectrometer, wherein
    the controller determines, on the basis of the result of the evaluation and the instruction information input by the switch, whether to adopt the result of the measurement performed by the spectrometer,
    the controller evaluates, by comparing a pre-set threshold or a pre-set acceptable range with the operation result, whether the results of the measurement performed by the spectrometer are valid,
    even when the instruction information is input by the switch, the controller does not adopt the results of the measurement if the results of the measurement are invalid,
    when the controller determines the results of the measurement are to be adopted, the controller further performs an operation to obtain a characteristic value of the living tissue on the basis of a measurement result that is the last of the results of the measurement determined to be adopted out of the results of the measurement determined to be valid, and
    the output processor outputs the characteristic value obtained by the controller on the basis of the last of the results of the measurement.

2. The optical measurement apparatus according to claim 1, further comprising:
    a main body device that is provided with the light source, the spectrometer, the controller, the output processor, and the switch; and
    a probe attachable to and detachable from the main body device, the probe including an irradiation fiber for transferring the light supplied by the light source to emit the light to the living tissue and a light receiving fiber for receiving at least one of the reflection light and the scattering light from the living tissue to output at least one of the reflection light and the scattering light to the spectrometer.

3. An endoscope system comprising:
    an endoscope that includes a channel provided internally, the endoscope configured to capture an image at a distal end portion;
    an optical measurement apparatus that includes a probe having a distal end that is configured to be inserted into a subject via the channel of the endoscope and a main body to which the probe is detachably attached, the main body comprising:
        a light source configured to emit irradiation light to the living tissue;

a spectrometer configured to measure at least one of reflection light and scattering light from the living tissue;

a controller configured to perform a validity evaluation operation process on the basis of results of the measurement performed by the spectrometer, and to evaluate, on the basis of an operation result for validity evaluation, whether the results of the measurement performed by the spectrometer are valid;

an output processor configured to output at least a result of the evaluation performed by the controller; and a switch configured to input instruction information containing an instruction to adopt the results of the measurement performed by the spectrometer, wherein the controller determines, on the basis of the result of the evaluation and the instruction information input by the switch, whether to adopt the results of the measurement performed by the spectrometer;

a second light source configured to supply light to irradiate an imaging field of the endoscope;

a signal processor configured to process a signal of the image captured by the endoscope; and a display configured to display the image processed by the signal processor, wherein the probe includes an irradiation fiber for transferring the light supplied by the light source to emit the light to the living tissue and a light receiving fiber for receiving at least one of the reflection light and the scattering light from the living tissue to output at least one of the reflection light and the scattering light to the spectrometer, the controller evaluates, by comparing a pre-set threshold or a pre-set acceptable range with the operation result, whether the results of the measurement performed by the spectrometer are valid, even when the instruction information is input by the switch, the controller does not adopt the results of the measurement if the controller evaluates the results of the measurement as being invalid, when the controller determines the results of the measurement are to be adopted, the controller further performs an operation to obtain a characteristic value of the living tissue on the basis of a measurement result that is the last of the results of the measurement determined to be adopted out of the results of the measurement determined to be valid, the output processor outputs, to the display, the characteristic value obtained by the controller on the basis of the last results of the measurement, and the display displays the characteristic value that is obtained by the controller on the basis of the last of the results of the measurement and that is output by the output processor.

4. The endoscope system according to claim 3, wherein the output processor outputs the result of the evaluation performed by the controller to the display; and the display displays the result of the evaluation performed by the controller, the result being output by the output processor.

5. A non-transitory computer-readable storage medium with an executable program stored thereon, wherein the program instructs a processor of an optical measurement apparatus for measuring an optical characteristic of a living tissue to perform:

causing a light source to emit light to the living tissue and measuring, using a spectrometer, at least one of reflection light and scattering light from the living tissue;

performing a validity evaluation operation process on the basis of results of the measuring;

evaluating, on the basis of an operation result for validity evaluation whether the results of the measuring are valid;

outputting, by an output device, at least a result of the evaluating;

inputting, through an input device, instruction information containing an instruction to adopt the results of the measuring; and determining, on the basis of the result of the evaluating and the instruction information, whether to adopt the result of the measuring, wherein by comparing a pre-set threshold or a pre-set acceptable range with the operation result, it is evaluated whether the results of the measurement performed by the spectrometer are valid, even when the instruction information is input, the results of the measurement are not adopted if the results of the measurement are invalid, and when the results of the measurement are to be adopted, performing an operation to obtain a characteristic value of the living tissue on the basis of a measurement result that is the last of the results of the measuring determined to be adopted out of the results of the measuring determined to be valid by the validity evaluator, and outputting the characteristic value.

* * * * *